(12) United States Patent
Kim et al.

(10) Patent No.: US 9,376,354 B2
(45) Date of Patent: Jun. 28, 2016

(54) DISPLACEMENT DESORPTION PROCESS FOR LIGHT OLEFIN SEPARATION

(75) Inventors: Jong Nam Kim, Daejeon (KR); Jong Ho Park, Daejeon (KR); Hee Tae Beum, Daejeon (KR); Seong Jun Lee, Daejeon (KR); Jang Jae Lee, Seongnam-si (KR); Dong Wook Kim, Daejeon (KR); Chang Hyun Ko, Daejeon (KR); Sang Sup Han, Daejeon (KR); Soon Haeng Cho, Daejeon (KR)

(73) Assignees: KOREA INSTITUTE OF ENERGY RESEARCH, Daejeon (KR); SK INNOVATION CO., LTD., Seoul (KR)

( * ) Notice: Subject to any disclaimer, the term of this patent is extended or adjusted under 35 U.S.C. 154(b) by 542 days.

(21) Appl. No.: 13/819,007

(22) PCT Filed: Aug. 26, 2011

(86) PCT No.: PCT/KR2011/006327
§ 371 (c)(1),
(2), (4) Date: Apr. 15, 2013

(87) PCT Pub. No.: WO2012/026786
PCT Pub. Date: Mar. 1, 2012

(65) Prior Publication Data
US 2013/0206581 A1     Aug. 15, 2013

(30) Foreign Application Priority Data
Aug. 26, 2010   (KR) .................. 10-2010-0082775

(51) Int. Cl.
*B01D 53/04* (2006.01)
*C07C 7/04* (2006.01)
*C07C 7/13* (2006.01)
*C07C 7/00* (2006.01)

(52) U.S. Cl.
CPC ............... *C07C 7/005* (2013.01); *B01D 53/04* (2013.01); *C07C 7/04* (2013.01); *C07C 7/13* (2013.01);

(Continued)

(58) Field of Classification Search
None
See application file for complete search history.

(56) References Cited

U.S. PATENT DOCUMENTS 6,293,999 B1   9/2001  Cheng et al.
6,488,741 B2   12/2002 Olson (Continued)

FOREIGN PATENT DOCUMENTS

EP   0708070 A1   4/1996
JP   61-126036 A  6/1986

(Continued)

OTHER PUBLICATIONS

JPO Office Action for Japanese Patent Application No. 2013-525839 which corresponds to the above-identified U.S. application.

(Continued)

*Primary Examiner* — Tam M Nguyen
(74) *Attorney, Agent, or Firm* — LRK Patent Law Firm

(57) ABSTRACT

A process and apparatus for separating an olefin from mixed gases containing light olefins is provided. The process includes adsorbing the olefin of an olefin-containing mixed gas in an adsorption column packed with an adsorbent selectively adsorbing the olefin; discharging gases other than the olefin through the outlet of the adsorption column; desorbing the adsorbed olefin by displacement using a desorbent, and separating the olefin from the desorbent, thereby producing a high-purity olefin. The apparatus includes adsorption columns packed with an adsorbent selectively adsorbing an olefin, and at least two distillation columns for separating an olefin/desorbent mixture and an olefin poor stream/desorbent into their components. If the olefin concentration of the off-gas from an olefin rinse step is higher than that of a raw material gas, recovering the olefin from the off-gas is carried out before or after the adsorption step.

7 Claims, 2 Drawing Sheets

(52) U.S. Cl.
CPC ....... *B01D 2253/108* (2013.01); *B01D 2256/24* (2013.01); *B01D 2257/7022* (2013.01); *B01D 2259/404* (2013.01); *B01D 2259/40086* (2013.01); *Y02P 30/464* (2015.11)

(56) References Cited

U.S. PATENT DOCUMENTS

| | | |
|---|---|---|
| 6,867,166 B2 | 3/2005 | Yang et al. |
| 2010/0048971 A1 | 2/2010 | Kim et al. |

FOREIGN PATENT DOCUMENTS

| | | |
|---|---|---|
| JP | 06-079123 A | 3/1994 |
| JP | 07-207280 A | 8/1995 |
| JP | 2009-531368 A | 9/2009 |
| KR | 10-0822847 B1 | 4/2008 |
| KR | 10-0849987 B1 | 8/2008 |
| WO | 2008/120921 A1 | 10/2008 |

OTHER PUBLICATIONS

International Search Report for PCT Application No. PCT/KR2011/006327 filed Aug. 26, 2011.

| Time | t1 | t2 | t3 | t4 |
|---|---|---|---|---|
| AD1 | Adsorption | Recovery | Olefin rinse | Desorption |
| AD2 | Desorption | Adsorption | Recovery | Olefin rinse |
| AD3 | Olefin rinse | Desorption | Adsorption | Recovery |
| AD4 | Recovery | Olefin rinse | Desorption | Adsorption |

| Time | t1 | t2 | t3 | t4 |
|---|---|---|---|---|
| AD1 | Recovery | Adsorption | Olefin rinse | Desorption |
| AD2 | Desorption | Recovery | Adsorption | Olefin rinse |
| AD3 | Olefin rinse | Desorption | Recovery | Adsorption |
| AD4 | Adsorption | Olefin rinse | Desorption | Recovery |

DISPLACEMENT DESORPTION PROCESS FOR LIGHT OLEFIN SEPARATION

TECHNICAL FIELD

The present invention relates to a process and apparatus for recovering a high-purity olefin in concentration from mixed gases containing light olefins (ethylene, propylene, etc.), such as an ethylene/ethane mixed gas, propylene/propane mixed gas, fluidized catalytic cracking (FCC) off-gas, polyethylene (PE) off-gas, or polypropylene (PP) off-gas.

BACKGROUND ART

Distillation techniques have been used to separate olefin/paraffin mixtures such as an ethylene/ethane mixture or propylene/propane mixture. In such distillation techniques, because there is a small difference in boiling point between olefin and paraffin, distillation columns having a large number of distillation trays are used, thus incurring high energy and equipment costs. Although the off-gas from fluidized catalytic cracking (FCC) processes which produce gasoline and propylene by treating the atmospheric residue or vacuum residue generated in crude oil refining processes contains about 20 vol % of ethylene, the concentration of ethylene in the FCC off-gas is low and the FCC off-gas contains various gases. For this reason, ethylene has not yet been recovered from the FCC off-gas in an economic manner, and the FCC off-gas has been used as fuel gas.

In recent years, technology for reducing olefin separation costs by using a process of separating olefins by adsorption has been studied as a substitute for processes of separating olefins by distillation.

Conventional techniques of separating light olefins (ethylene, propylene, butylene, etc.) and paraffins (ethane, propane, butane, etc.) by adsorption are as follows.

U.S. Pat. No. 6,867,166 discloses a technique of separating olefins by a pressure swing adsorption or temperature swing adsorption process using a transition metal ion-supported adsorbent having selectivity for ethylene or propylene.

Also, U.S. Pat. No. 6,293,999 discloses a technique of separating propylene from a propane/propylene mixed gas by a pressure swing adsorption or temperature swing adsorption process using an ALPO-14 adsorbent having a molecular sieve function which selectively adsorbs only propylene. Moreover, U.S. Pat. No. 6,488,741 discloses a technique of separating C2-C4 olefins by a pressure swing adsorption process or a combination of a pressure swing adsorption process with a distillation process using a zeolite adsorbent. In addition, U.S. Pat. No. 6,488,741 discloses a technique of separating propylene from a propane/propylene mixed gas using an 8-member ring adsorbent having a molecular sieve function, such as SAPO.

As described above, the processes for separating ethylene or propylene by adsorption are carried out by gas-phase adsorption rather than liquid-phase adsorption, because ethylene or propylene is not easy to liquefy. Also, the regeneration of adsorbents is performed by pressure swing adsorption or temperature swing adsorption. Elevating and lowering the temperature of an adsorption column in the temperature swing adsorption process requires a lot of time, so that the productivity of the bulk gas separation process is low, and thus the equipment cost is high. The pressure swing adsorption or vacuum swing adsorption process is not suitable for separating large amounts of mixed gases, because compressors and vacuum pumps have limited capacities.

Korean Patent Registration No. 0849987 registered in the name of the applicant discloses an adsorption/separation process capable of separating ethylene from an FCC off-gas containing a low concentration of ethylene using an ethylene-selective adsorbent. The disclosed process is a displacement desorption process of desorbing adsorbed ethylene using a desorbent and is a technique of concentrating and recovering ethylene from the FCC off-gas through the sequential steps of adsorption, ethylene rinse and displacement desorption. Also, Korean Patent Registration No. 0822847 discloses a displacement desorption process for separating a C4 olefin from paraffin, which comprises an adsorption step, a C4 olefin rinse step and a desorption step.

The above-described olefin/paraffin displacement desorption process is based on adsorption-olefin rinse-desorption steps. In this process, the amount of olefin which is discharged out of the adsorption column in a rinse step is increased depending on the concentration of olefin in the raw material, the adsorption properties of olefin and paraffin, and the required concentration of olefin in products, thus reducing the recovery rate of olefin.

The present invention provides a displacement desorption process that increases both the recovery of olefin and the economic efficiency of the process by recovering olefin which is discharged in the adsorption and rinse steps.

DISCLOSURE OF INVENTION

Technical Problem

It is an object of the present invention to provide a process and apparatus for separating a high-purity olefin from mixed gases containing light olefin (ethylene, propylene, etc.), such as an ethylene/ethane mixed gas, a propylene/propane mixed gas, fluidized catalytic cracking off-gas, polyethylene off-gas, and polypropylene off-gas, at a high rate of recovery.

Because a conventional displacement desorption process is based on adsorption-olefin rinse-desorption steps, olefin is discharged out of the adsorption column in the adsorption and olefin rinse steps, thus reducing the recovery of olefin. The present invention provides a displacement desorption process improving an olefin recovery rate further comprising before or after the adsorption step, introducing a gas discharging from adsorption or olefin rinse step into the adsorption column, thereby recovering an olefin from the discharged gas.

In the above-described conventional technology, the amount of olefin that is discharged out of the adsorption column in the adsorption and rinse steps is large so that the recovery of olefin and the economic efficiency of the process are not high. The present invention provides a process of separating ethylene by adsorption, in which ethylene which is discharged in the adsorption and rinse steps is recovered to increase the recovery of ethylene and the economic efficiency of the process.

BRIEF DESCRIPTION OF DRAWINGS

The above and other objects, features and advantages of the present invention will be more clearly understood from the following detailed description taken in conjunction with the accompanying drawing, in which.

MODE FOR THE INVENTION

The displacement desorption process of the present invention either comprises the sequential steps of adsorption, recovery, olefin rinse and desorption or comprises the sequential steps of recovery, adsorption, olefin rinse and desorption. Hereinafter, one aspect of the invention will be described with reference to FIG. 1.

In the improved displacement desorption process for recovering an olefin according to the present invention, the sequential steps of adsorption, recovery, rinse and desorption or the sequential steps of recovery, adsorption, rinse and desorption are repeatedly carried out in an apparatus comprising a plurality of adsorption columns packed with an adsorbent selectively adsorbing the olefin, and at least two distillation columns, including a distillation column for separating an olefin-rich stream from a desorbent and a distillation column for separating an olefin-poor stream from a desorbent, thereby separating a high-purity olefin from an olefin-containing mixed gas.

The method for separating an olefin from an olefin-containing mixed gas using at least one adsorption column and at least two distillation columns comprises the steps of:

i) adsorption step: introducing the olefin-containing mixed gas into an adsorption column packed with an olefin selective adsorbent to adsorb an olefin from the mixed gas, and sending unadsorbed components and a desorbent, fed into the adsorption column during desorption, through the outlet of the adsorption column to a distillation column for separating an olefin poor stream/desorbent mixture into components;

ii) rinse step: introducing a high-concentration olefin, obtained from a distillation column for separating an olefin from a desorbent, into the adsorption column, thereby removing paraffin and other gases from the adsorption column to increase the purity of the olefin in the adsorption column; and iii) desorption step: introducing a desorbent into the adsorption column that was subjected to step ii), to desorb the olefin from the adsorption column, and then sending the olefin/desorbent mixture to a distillation column for separating the olefin/desorbent mixture into components, thereby producing a high-purity olefin; and before or after the step i), iv) recovery step: introducing a gas (olefin-containing gas) resulting from olefin rinse into the adsorption column, thereby recovering an olefin from the olefin-containing gas.

Also, the steps i) to iv) may be repeatedly carried out in a plurality of adsorption columns.

Preferably, a plurality of adsorption columns having different process configurations may be repeatedly carried out in each step to improve processing efficiency.

Figures 1, 2:
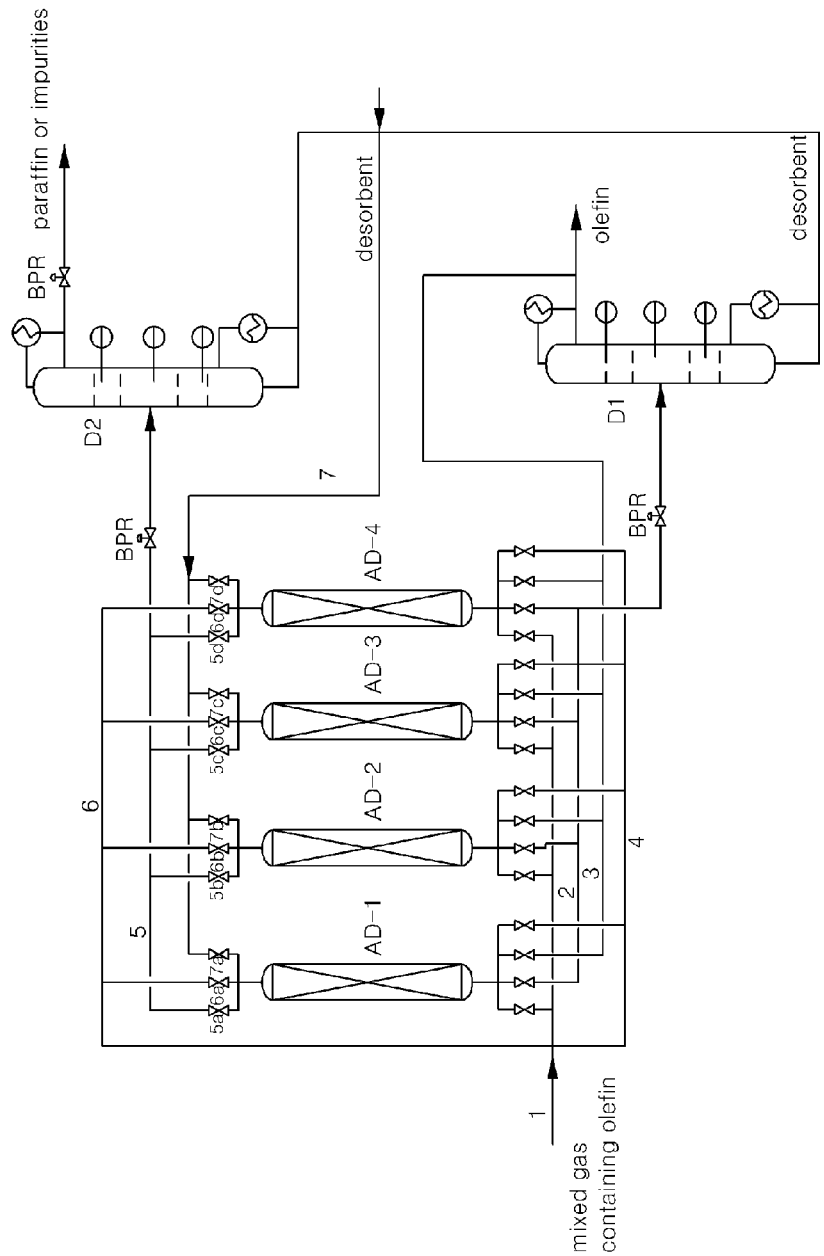
FIG. 1 is a schematic view showing a process and apparatus for recovering a high-concentration olefin from an olefin-containing mixed gas according to the present invention, in which the apparatus comprises four adsorption columns (AD-1, AD-2, AD-3 and AD-4) which selectively adsorb an olefin, and two distillation columns (D1 and D2) which separate an olefin/desorbent mixture and a paraffin-containing gas/desorbent into their components.
FIG. 2 is a schematic view showing the one-cycle operation of displacement desorption process for olefin separation by the steps of recovery, adsorption, recovery, rinse and desorption.
Figures 3, 4:
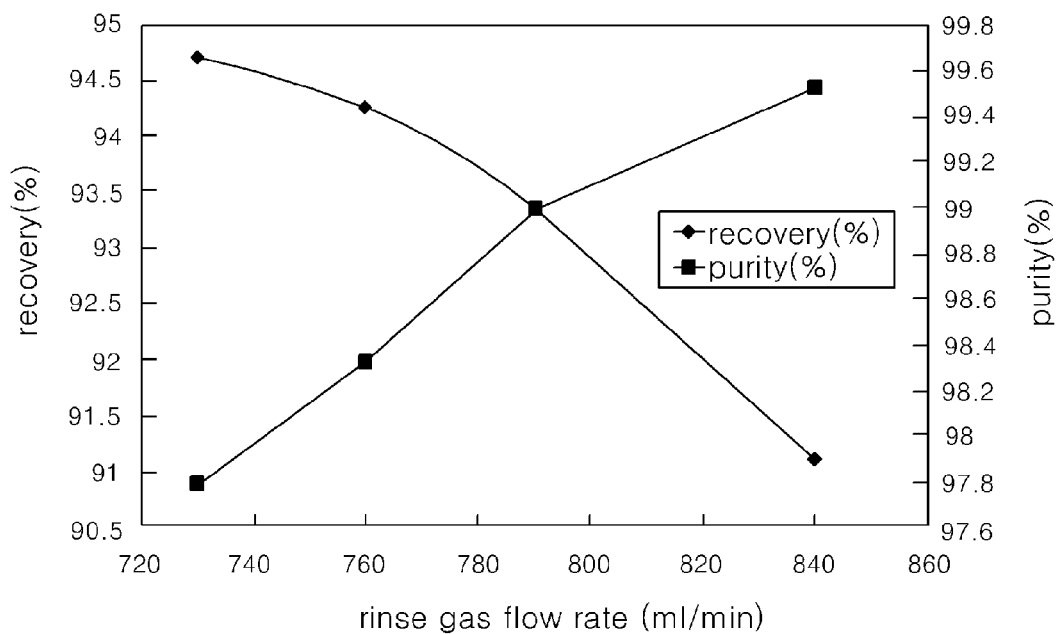
FIG. 3 is a schematic view showing the one-cycle operation of displacement desorption process for olefin separation by the steps of recovery, adsorption, rinse and desorption.
FIG. 4 is a graph showing the purity and recovery rate of ethylene in a product obtained in Example 1 of the present invention, carried out to separate ethylene from a raw material gas having a composition similar to that of fluidized catalytic cracking (FCC) off-gas by a displacement desorption process.

As shown in FIGS. 2 and 3 below, in one embodiment, the process of recovering a high-concentration olefin from the olefin-containing mixed gas using the displacement desorption process can be done by carrying out the recovery, adsorption, olefin rinse and desorption steps in four adsorption columns (AD-1, AD-2, AD-3 and AD-4).

As the ethylene selective adsorbent, a π-complex adsorbent selectively forming a π-complex with olefin, a zeolite X adsorbent, a zeolite Y adsorbent or a zeolite A adsorbent may be used. Preferably, a zeolite 13x adsorbent may be used.

The adsorption or desorption step may be preferably carried out under conditions of a pressure of 1-30 atm and a temperature of 20~150° C.

The desorbent separated by the distillation column for separating the olefin-poor stream/desorbent mixture and by the distillation column for separating the olefin rich stream/desorbent mixture may be recycled to the adsorption column.

The desorbent that is used in the present invention varies depending on the kind of olefin in the olefin-containing mixed gas and may be mainly a C3-C6 hydrocarbon, but is not limited thereto.

In one embodiment of the present invention, an apparatus for selectively separating an olefin from an olefin-containing mixed gas by displacement desorption comprises a plurality of adsorption columns packed with an adsorbent that selectively adsorbs the olefin; and at least two distillation columns, including a distillation column (D1) for separating an olefin rich stream/desorbent mixture into components, and a distillation column (D2) for separating an olefin poor stream/desorbent into components. The plurality of adsorption columns are connected with an olefin-containing mixed gas supply pipeline, an olefin rich stream/desorbent discharge pipeline leading to a distillation column (D1) for separating olefin rich stream/desorbent into components, and a pipeline for supplying a given amount of an olefin-rich stream from the distillation column (D1); a pipeline for introducing a gas discharged from the step ii) into an adsorption column that was subjected to adsorption and a pipeline for guiding an olefin poor stream/desorbent mixture discharged from the step i); and a pipeline for supplying the desorbent, separated in the distillation columns (D1, D2), to the adsorption column.

In one embodiment of the present invention, as shown in FIG. 1 an apparatus for selectively separating an olefin from an olefin-containing mixed gas by displacement desorption may comprise four adsorption columns (AD-1, AD-2, AD-3 and AD-4) packed with an adsorbent selectively adsorbing the olefin, and two distillation columns, including a distillation column (D1) for separating an olefin-rich stream/desorbent mixture into components and a distillation column (D2) for separating an olefin-poor stream/desorbent mixture into components.

Referring to FIG. 1, the apparatus for selectively separating olefin from an olefin-containing mixed gas by displacement desorption comprises:

an olefin selective adsorbent-packed adsorption column AD-1 which is connected with an olefin-containing mixed gas supply pipeline via a valve 1a, is connected via a valve 2a with an olefin rich stream/desorbent discharge pipeline 2 leading to a distillation column D1, is connected via a valve 3a with a pipeline 3 for supplying a given amount of an olefin-rich stream from the distillation column D1, is connected via a valve 6a and a valve 4a with the pipeline 6 and the pipeline 4 for introducing a gas discharged from an olefin rinse step into an adsorption column that was subjected to adsorption, is connected via a valve 5a with a pipeline 5 for guiding an olefin poor stream/desorbent mixture discharged from the adsorption step, and is connected via a valve 7a with a pipeline 7 for supplying the desorbent, separated in the distillation column D1 and the distillation column D2, to the adsorption column;

an olefin selective adsorbent-packed adsorption column AD-2 which is connected with an olefin-containing mixed gas supply pipeline via a valve 1b, is connected via a valve 2b with an olefin rich stream/desorbent discharge pipeline 2 leading to a distillation column D1, is connected via a valve 3b with a pipeline 3 for supplying a given amount of an olefin-rich stream from the distillation column D1, is connected via a valve 6b and a valve 4b with the pipeline 6 and the pipeline 4 for introducing a gas discharged from an olefin rinse step into an adsorption column having subjected to adsorption, is connected via a valve 5b with a pipeline 5 for guiding an olefin poor stream/desorbent mixture discharged from the adsorption step, and is connected via a valve 7b with a pipeline 7 for supplying the desorbent, separated in the distillation column D1 and the distillation column D2, to the adsorption column;

an olefin selective adsorbent-packed adsorption column AD-3 which is connected with an olefin-containing mixed gas supply pipeline via a valve 1c, is connected via a valve 2c with an olefin rich stream/desorbent discharge pipeline 2 leading to a distillation column D1, is connected via a valve 3c with a pipeline 3 for supplying a given amount of an olefin-rich stream from the distillation column D1, is connected via a valve 6c and a valve 4c with a pipeline 6 and pipeline 4 for introducing a gas discharged from an olefin rinse step into an adsorption column that was subjected to adsorption, is connected via a valve 5c with a pipeline 5 for guiding an olefin poor stream/desorbent mixture discharged from the adsorption step, and is connected via a valve 7c with a pipeline 7 for supplying the desorbent, separated in the distillation column D1 and the distillation column D2, to the adsorption column;

an olefin selective adsorbent-packed adsorption column AD-4 which is connected with an olefin-containing mixed gas supply pipeline via a valve 1d, is connected via a valve 2d with an olefin rich stream/desorbent discharge pipeline 2 leading to a distillation column D1, is connected via a valve 3d with a pipeline 3 for supplying a given amount of an olefin-rich stream from the distillation column D1, is connected via a valve 6d and a valve 4d with the pipeline 6 and the pipeline 4 for introducing a gas discharged from an olefin rinse step into an adsorption column that was subjected to adsorption, is connected via a valve 5d with a pipeline 5 for guiding an olefin poor stream/desorbent mixture discharged from the adsorption step, and is connected via a valve 7d with a pipeline 7 for supplying the desorbent, separated in the distillation column D1 and the distillation column D2, to the adsorption column; and at least two distillation columns, including a distillation column D1 for separating an olefin rich stream/desorbent mixture into components and a distillation column D2 for separating an olefin poor stream/desorbent mixture into components;

wherein the adsorption, recovery, olefin rinse and desorption steps may be repeatedly carried out in the four adsorption columns.

At this time, each of adsorption columns having different process configurations may be repeatedly carried out in each step to improve processing efficiency. Hereinafter, in one embodiment, the one-cycle operation of the process of selectively separating an olefin from an olefin-containing mixed gas by displacement desorption will be described with reference to FIG. 2.

First, an adsorption step is carried out in which an olefin-containing mixed gas is introduced through the pipeline 1 and the valve 1a into the adsorption column AD-1 so that the olefin is adsorbed, and the desorbent remaining in the adsorption column and the olefin-poor gas are fed into the distillation column D2 through the valve 5a and the pipeline 5 to recover the desorbent. While the adsorption column AD-1 undergoes the adsorption step, the adsorption column AD-2 is subjected to a desorption step in which the adsorption column AD-2 is fed with the desorbent through the pipeline 7 and the valve 7b to desorb the adsorbed olefin. The olefin rich stream which is discharged together with the desorbent is introduced into the distillation column D1 through the valve 2b and the pipeline 2 so that a high-purity olefin is separated from the desorbent. The desorbent used is one obtained from the bottom of the distillation columns D1 and D2. At the same time, the adsorption column AD-3 undergoes an olefin rinse step in which a portion of a high-purity olefin from the distillation column D1 is introduced into the adsorption column AD-3 through the pipeline 3 and the valve 3c so that trace amounts of paraffin and other gases adsorbed together with olefin are removed, thus increasing the purity of olefin. The gas discharged from the adsorption column AD-3 is passed sequentially through the valve 6c, the pipeline 6, the pipeline 4 and the valve 4d to the adsorption column AD-4 in which the olefin contained in the discharged gas is recovered by adsorption, and gases other than the olefin are fed into the distillation column D2 through the valve 5d and the pipeline 5 (recovery step).

As shown in Table 1 above, when the adsorption step in the adsorption column AD-1 has completed, the adsorption column AD-1 is subjected to the recovery step for adsorbing the olefin component from the gas discharged from the adsorption column AD-4 (ethylene rinse step), and the adsorption column AD-2 that was subjected to the desorption step undergoes the adsorption step of adsorbing an olefin from an olefin-containing raw material gas introduced into the adsorption column AD-2. At the same time, the adsorption column AD-3 undergoes the desorption step of desorbing the adsorbed olefin with the desorbent, and the adsorption column AD-4 is subjected to the rinse step wherein small amounts of paraffin and other gases are removed along with the high-concentration olefin obtained in the distillation column D1 and the concentration of olefin is increased. When one adsorption column is subjected to the adsorption step-recovery step-olefin rinse step-desorption step as described above, one cycle of the operation has completed and is followed by the next cycle.

Also, as shown in Table 2 above, the process for selectively separating an olefin from an olefin-containing mixed gas by displacement desorption may be operated in the order of recovery step-adsorption step-olefin rinse step-desorption step depending on the olefin concentration of the mixed gas and the olefin purity of a desired product. Specifically, the process for selectively separating an olefin from an olefin-containing mixed gas by displacement desorption may also be done in order of the recovery step of introducing the gases discharged from the adsorption and olefin rinse steps into the adsorption column that was subjected to desorption, thereby recovering an olefin from the exhausted gases, the adsorption step of introducing an olefin-containing raw material gas into the adsorption column that was subjected to the recovery step, thereby adsorbing an olefin from the raw material gas, the olefin rinse step of introducing a portion of a high-concentration olefin obtained from the distillation column D2 into the adsorption column that was subjected to the adsorption step, thereby removing impurities from the adsorption column and increasing the purity of olefin in the adsorption column, and the desorption step of introducing a desorbent into the adsorption column that was subjected to the olefin rinse step, thereby desorbing the olefin from the adsorption column.

In addition, when the pressure of the adsorption step is higher than atmospheric pressure, the ethylene process for selectively separating an olefin from an olefin-containing mixed gas by displacement desorption may further comprise, before the recovery step, a cocurrent depressurization step of discharging components other than an olefin from the adsorption column.

Hereinafter, preferred examples of the present invention will be described in detail.

Example 1

A displacement desorption process for separating an olefin from an olefin-containing mixed gas was operated according to the configuration shown in Table 1 above using the inventive apparatus for separating an olefin from an olefin-containing mixed gas as shown in FIG. 1. As shown in Table 3 below, the composition of a raw material used in the experiment was similar to that of fluidized catalytic cracking (FCC) off-gas and had an ethylene concentration of 19.6%. Zeolite X was used as an adsorbent for ethylene separation, and a C4 mixed gas (85% isobutane and 15% n-butane) was used as a desorbent. The adsorption step was done at 80° C. and 8 bar, and as ethylene required for the high-purity ethylene rinse, commercially available high-purity ethylene (99.95%) was used.

TABLE 1

| Raw material gas | Composition (vol %) |
| --- | --- |
| Hydrogen | 21.0 |
| Nitrogen | 14.4 |
| Methane | 30.7 |
| Ethane | 12.2 |
| Ethylene | 19.6 |
| Propane | 0.2 |
| Propylene | 1.9 |

Table 2 below shows the concentration of ethylene discharged from the ethylene rinse step when the process was done according to the above-described configuration under the above conditions. As can be seen in Table 4, ethylene was discharged at concentrations higher than the concentration of ethylene in the raw material, suggesting that, when the discharged ethylene is discarded without being recovered, the high recovery rate of ethylene cannot be achieved. FIG. 2 shows the purity and recovery rate of ethylene obtained by the experiment. As shown in FIG. 2, the flow rate of ethylene rinse gas used in the operation was 840 ml/min, 99.5 vol % ethylene could be separated from the raw material at a recovery rate of 91%.

TABLE 2

| Flow rate (ml/min) of ethylene rinse gas | Ethylene concentration (vol %) of gas discharged from ethylene rinse step |
| --- | --- |
| 730 | 35.3 |
| 760 | 27.0 |
| 790 | 30.2 |
| 840 | 41.2 |

<Concentration of Ethylene in Gas Discharged from Ethylene Rinse Step>

A conventional displacement desorption process for recovering an olefin from an olefin-containing mixed gas does not contain a recovery step capable of efficiently recovering an olefin from the gas discharged from the olefin rinse step. Thus, when the concentration of olefin in the gas discharged from the olefin rinse step is higher than the concentration of olefin in a raw material gas, a large amount of olefin is lost, thus reducing the recovery rate of olefin. On the other hand, in the present invention, the recovery step is carried out before or after the adsorption step to recover an olefin from the gas discharged from the olefin rinse step, and thus an olefin recovery rate higher than that of the conventional process can be achieved.

Although the preferred embodiments of the present invention have been described for illustrative purposes, those skilled in the art will appreciate that various modifications, additions and substitutions are possible, without departing from the scope and spirit of the invention as disclosed in the accompanying claims.

The invention claimed is:

1. A method for separating an olefin from an olefin-containing mixed gas using at least one adsorption column and at least two distillation columns including a distillation column that separates an olefin rich stream and a desorbent and a distillation column that separates an olefin poor stream and a desorbent, the method comprising:

i) adsorption step: introducing the olefin-containing mixed gas into an adsorption column packed with an olefin selective adsorbent to adsorb an olefin from the mixed gas, and discharging unadsorbed components and a desorbent retained in the adsorption column at a desorption step to the outlet of the adsorption column and then discharging them to the distillation column that separates an olefin poor stream and a desorbent;

ii) rinse step: introducing a high-concentration olefin, obtained from the distillation column that separates an olefin rich stream and a desorbent, into the adsorption column, thereby removing paraffin and other gases from the adsorption, column to increase the purity of the olefin in the adsorption column;

iii) desorption step: introducing the desorbent, which was separated from the distillation columns in the steps i) and ii), or another desorbent, which is introduced independently of the desorbent separated in the steps i) and ii), into the adsorption column having been subjected to the step ii), to desorb the olefin from the adsorption column so as to form an olefin/desorbent mixture, and then sending the olefin/desorbent mixture to the distillation column that separates an olefin rich stream and a desorbent, thereby producing a high-purity olefin; and before or after the step i), iv) recovery step: introducing an olefin-containing gas discharged from the rinse step into the adsorption column, thereby recovering an olefin from the olefin-containing gas.

2. The process of claim 1, wherein the steps i) to iv) are repeatedly carried out in a plurality of adsorption columns.

3. The method of claim 1, wherein, if the pressure of step i) is higher than atmospheric pressure, the process further comprises, before step ii), a step of discharging components other than olefin from the adsorption column by cocurrent pressurization.

4. The method of claim 1, wherein the olefin selective adsorbent is a π-complex adsorbent selectively forming a π-complex with ethylene, a zeolite X adsorbent, a zeolite Y adsorbent or a zeolite A adsorbent.

5. The method of claim 1, wherein the desorbent is a C3-C6 hydrocarbon.

6. The method of claim 1, wherein step i) or iii) is carried out under conditions of a pressure of 1-30 atm and a temperature of 20~150° C.

7. The method of claim 1, wherein the desorbent separated in the distillation column for separating the olefin-poor stream/desorbent mixture and in the distillation column for separating the olefin rich stream/desorbent mixture is recycled to the adsorption column.

* * * * *